United States Patent [19]
Heinemann et al.

[11] Patent Number: 5,502,066
[45] Date of Patent: Mar. 26, 1996

[54] 1,2,4-DITHIAZOLIUM SALTS AS CHEMOTHERAPEUTICS

[75] Inventors: Ulrich Heinemann, Leichlingen; Ralf Tiemann, Leverkusen; Klaus Stünkel, Wuppertal, all of Germany

[73] Assignee: Bayer Aktiengesellschaft, Leverkusen, Germany

[21] Appl. No.: 258,118

[22] Filed: Jun. 10, 1994

[30]     Foreign Application Priority Data

Jun. 18, 1993 [DE] Germany .......................... 43 20 157.1

[51] Int. Cl.$^6$ ........................ A61K 31/41; C07D 285/01
[52] U.S. Cl. ........................ 514/360; 514/212; 514/236.8; 514/252; 514/326; 514/342; 548/123
[58] Field of Search ........................... 548/123; 514/360, 514/326, 236.8, 252, 342, 212

[56]              References Cited

U.S. PATENT DOCUMENTS 3,888,872  6/1975  Bellina ................................... 548/123

FOREIGN PATENT DOCUMENTS

| | | |
|---|---|---|
| 2219992 | 11/1972 | Germany . |
| 2222201 | 12/1972 | Germany . |
| WO9110649 | 7/1991 | WIPO . |
| WO9404517 | 3/1994 | WIPO . |

OTHER PUBLICATIONS

Journal of Medicinal Chemistry, 1972, vol. 15, No. 3, pp. 315–320; "Insect Chemosterilants. 11. Substituted 3,5–Diamino–1,2,4–dithiazolium Salts and Related Compounds", J. E. Oliver et al.
J. Org. Chem., vol. 36, No. 22, 1971, pp. 3465–3467; "The Reaction of Dithiazolium Cations with Sodium Azide", J. E. Oliver.
Chemical Abstracts, Agricultural Chemistry, p. 6; 54562C/31, J5 5081–804; "Agricultural miticide and fungicide composition . . . ", Nihon Tokushu Noyaku Sei, Dec. 15, 1978.
Chemical Abstracts, Agricultural Chemistry, p. 3; 10267 J/51, J5 7183–770; "Amino–substd. dithiazole drivs . . . ", Nihon Tokushu Noyaku Sei, May 1, 1981.
Soc. Chim., 5$^e$ serie, 1978, II, Memoires, pp. 481–484; "Automatisation de la preparation au laboratoire du chlorure de . . . ", A. Delcaroix et al., Nov. 21, 1977.
1987 The Chemical Society of Japan, Bull. Chem. Soc., Jpn, vol. 60, pp. 2686–2688, No. 7; "The Synthesis of Heteroaromatic Cations . . . ", I. Shibuya et al.
J. Amer. Chem. Soc, vol. 80, pp. 414–417, Aug. 5, 1957; "The Structure and Antimicrobial Activity of some Isothiocyanate . . . ", C. K. Bradsher et al.
Proc. Natl. Acad. Sci. USA, vol. 76, 1979, pp. 5939–5943; "Galactosamine–induced sensitization to the lethal effects of endotoxin", C. Galanos et al.
J. Exp. Med., The Rockefeller University Press, vol. 165, Mar. 1987; pp. 657–663; "Lethal Toxicity of Lipopolysaccharide . . . " V. Lehmann et al.
Journal of Economic Entomology, vol. 65, No. 2, Apr. 1972; "Chemosterilization of Male House Flies with Dithiazolium . . . " S. C. Chang et al.
Adv. Intern. Medi., vol. 35, 1990, pp. 45–72; "Tumor Necrosis Factor: Immunologic, Antitumor, Metabolic, and . . . ", C. Grunfel et al.
Circulatory Shock, vol. 31, pp. 171–181, 1990; "Pentoxifylline Increases Survival in Murine Endotoxin Shock and Decreases . . . ", U. F. Schade.
Clin. Exp. Immunol., vol. 80, pp. 232–235, 1990; "Tetrandrine, a plant alkoloid, inhibits the production of . . . ", A. Ferrante et al.
J. Exp. Med., The Rockefeller University Press, vol. 173, Mar. 1991, pates 669–703; "Thalidomide Selectively Inhibits Tumor . . . ", E. P. Sampaio et al.
Infection and Immunity, May 1992, pp. 1941–1945, vol. 60, No. 5; "Colchicine prevents tumor necrosis factor–induced . . . ", G. Tiegs et al.
Journal of Medicinal Chemistry, 1972, vol. 15, No. 3, pp. 315–320; "Insect Chemosterilents. 1. Substituted 3,5–diamino–1,2,4–. . . ", J. E. Oliver et al.
Ann. Rev. Immunol, 1989, vol. 7, pp. 625–655; "The Biology of Cachectin/TNF–A Primary Mediator of the Host Response", B. Beutler et al.

*Primary Examiner*—Robert Gerstl
*Attorney, Agent, or Firm*—Sprung Horn Kramer & Woods

[57]              ABSTRACT

The invention relates to the use of 1,2,4-dithiazolium salts, some of which are known, of the general formula (I)

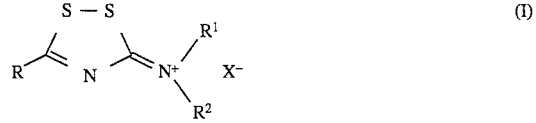

in which the substituents have the meaning given in the description, to a process for their preparation and to their use as chemotherapeutics, in particular as TNF inhibitors.

6 Claims, No Drawings

1,2,4-DITHIAZOLIUM SALTS AS CHEMOTHERAPEUTICS

The invention relates to the use of 1,2,4-dithiazolium salts, some of which are known, a process for their preparation and their use as chemotherapeutics.

It has been found that the 1,2,4-dithiazolium salts, some of which are known, of the general formula (I)

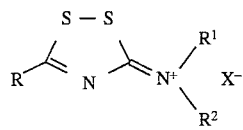

in which

R represents a radical of the formula —S—R³ or —NR⁴R⁵,

R¹ represents alkyl or aryl and

R² represents alkyl or

R¹ and R² together with the nitrogen atom to which they are bonded, represent an optionally substituted heterocyclic radical, which can optionally contain further heteroatoms, and X represents the anion of an inorganic acid, and wherein R³ represents optionally substituted alkyl, R⁴ represents in each case optionally substituted alkyl, alkenyl, alkynyl or aryl and R⁵ represents in each case optionally substituted alkyl or alkenyl, or R⁴ and R⁵, together with the nitrogen atom to which they are bonded, represent an optionally substituted heterocyclic radical, which can optionally contain further heteroatoms, have a good activity as chemotherapeutics and can be used, in particular, as TNF inhibitors.

Tumour necrosis factor α (TNF-α; cachectin) and β (TNF-β; lymphotoxin) are related proteins which are formed by activated macrophages or, respectively, activated lymphocytes (B. Beutler and A. Cerami, 1989, Annu. Rev. Immunol. 7: 625; C. Grunfeld and M. A. Palladine, 1990, Adv. Intern. Med. 35; 45). As has been demonstrated in the past, these cytokines are a constituent of various biological processes, such as immunoregulation, inflammation, cachexia, angiogenesis and septic shock.

The biological effects of TNF-α and TNF-β are mediated by specific receptors. Cloning experiments based on molecular biological methods have demonstrated the existence of two different TNF receptor types (TNF-R) of molecular size 55 kDa and 75 kDa, and in particular for two species, humans and mice. The two receptor types here are capable of binding both TNF-α and TNF-β as a ligand. More in-depth investigations have shown, however, that human TNF-α is exclusively the ligand for the murine TNF-R of molecular weight 55 kDa. Human TNF accordingly does not undergo binding with the 75 kDa TNF-R type of the mouse.

Various scientific reports in recent years have attempted to describe the individual role of the two TNF receptors. The results of the investigations originate mainly in the use of polyclonal and monoclonal antibodies which were directed against the soluble form of the two TNF-R types. According to these investigations, the following TNF-mediated biological functions can be associated with the 55 kDa TNF-R; cytotoxicity, fibroblast proliferation and prostaglandin E₂ synthesis. From first reports, the role of the 75 kDa TNF-R appears to be limited to growth stimulation of thymocytes and T-lymphocytes (possibly here also only subgroups of T-lymphocytes), and also to that of B-lymphocytes.

The pathogenesis of endotoxemic or septic shock seems to be predominantly TNF-dependent. This conclusion is based on various experimental observations:

1. Neutralizing anti-TNF-α antibodies prevent lung failure and death in mice and apes (baboons) as a result of endotoxin or *E. coli* administration.

2. Intravenous infusion of TNF-α leads to a toxicological pattern which does not differ from that of endotoxemia or Gram-negative sepsis.

Additional indications for the particular role of TNF in the shock event result from findings which demonstrate that, in animals and humans who have been given either endotoxin or a septic shock, the serum TNF levels were significantly increased in comparison with non-stressed individuals. In the case of severe sepsis, the increased serum TNF levels correlated with the occurrence of mortality.

Moreover, reports of results on the importance of inter-leukin-1(IL-1)-neutralizing principles (for example IL-1 receptor antagonist, IL-1 ra) for therapy of endotoxemic or septic shock and other indications are increasing.

Thanks to the development of potent antibacterial substances, significant advances have been achieved in recent years in the treatment of bacterial infections. Despite this, the number of cases of sepsis or mortality in recent years still seems unexpectedly high. The consequence of such observations is the attempt to develop new principles/methods which deviate from antibacterial chemotherapy. Partial successes have thus been achieved with a human monoclonal antibody against endotoxin in patients with septic shock. Treatment with the aid of a murine monoclonal anti-human TNF-α antibody is another therapeutic starting point for septic shock.

In addition to these activities in the field of biological agents in respect of TNF-α and IL-1 antagonists and blockers, there are reports on blocking of TNF synthesis or TNF-α receptor binding on the basis of substances with small molecules (pentoxifylline: U. Schade, 1990, Circ. Shock 31: 171; tetrandrine: A. Ferrante et al., 1990, Clin. Exp. Immunol. 80: 232; thalidomide: E. P. Sampaio et al., 1991, J. Exp. Med. 173: 699; colchicine: G. Tiegs et al., 1992, Infect. Immun. 60: 1941).

Formula (I) provides a general definition of the 1,2,4-dithiazolium salts which can be used according to the invention. Compounds of the formula (I) which can preferably be used are those in which R represents a radical of the formula —S—R³ or —NR⁴R⁵, r represents straight-chain or branched alkyl having 1 to 18 carbon atoms, or represents aryl having 6 to 10 carbon atoms which is optionally substituted once or several times by identical or different substituents, possible substituents in each case being:

Halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoxyiminoalkyl having in each case 1 to 4 carbon atoms in the individual alkyl parts and phenyl which is optionally substituted once or several times by identical or different substituents from the group comprising halogen and/or straight-chain or branched alkyl and/or straight-chain or branched alkoxy and/ or straight-chain or branched halogenoalkyl and/or straight-chain or branched halogenoalkoxy having in each case 1 to 4 carbon atoms and, optionally, 1 to 9 identical or different halogen atoms, and $R^2$ represents straight-chain or branched alkyl having 1 to 18 carbon atoms, or $R^1$ and $R^2$, together with the nitrogen atom to which they are bonded, represent a saturated five- to seven-membered heterocyclic radical which is optionally substituted once or several times by identical or different substituents and can optionally contain further heteroatoms—in particular nitrogen, oxygen and/or sulphur—possible substituents being:

Halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, and X represents the anion of an inorganic acid, and wherein $R^3$ represents straight-chain or branched alkyl having 1 to 18 carbon atoms, or represents arylalkyl having 6 to 10 carbon atoms in the aryl part and 1 to 4 carbon atoms in the straight-chain or branched alkyl part or heteroarylalkyl having 2 to 9 carbon atoms and 1 to 3 identical or different heteroatoms—in particular nitrogen, oxygen and/or sulphur—in the heteroaryl part and 1 to 4 carbon atoms in the straight-chain or branched alkyl part, in each case optionally substituted in the aryl part once or several times by identical or different substituents, possible substituents in each case being:

Halogen, cyano, nitro, carbamoyl, in each case straight-chain or branched alkyl, alkoxy or alkoxycarbonyl having in each case 1 to 4 carbon atoms or in each case straight-chain or branched halogenoalkyl or halogenoalkoxy having in each case 1 to 4 carbon atoms and 1 to 9 identical or different halogen atoms, $R^4$ represents in each case straight-chain or branched alkyl, alkenyl or alkynyl having in each case up to 18 carbon atoms, or represents straight-chain or branched halogenoalkyl having 1 to 8 carbon atoms and 1 to 17 identical or different halogen atoms, or represents in each case straight-chain or branched cyanoalkyl, dioxolanylalkyl, alkoxyalkyl or dialkylaminoalkyl having in each case 1 to 8 carbon atoms in the individual alkyl parts, or represents cycloalkylalkyl having from 3 to 8 carbon atoms in the cycloalkyl part and 1 to 18 carbon atoms in the straight-chain or branched alkyl part, or represents aryl having 6 to 10 carbon atoms, arylalkyl having 6 to 10 carbon atoms in the aryl part and 1 to 4 carbon atoms in the straight-chain or branched alkyl part or heteroarylalkyl having 2 to 9 carbon atoms and 1 to 3 identical or different heteroatoms—in particular nitrogen, oxygen and/or sulphur—in the heteroaryl part and 1 to 4 carbon atoms in the straight-chain or branched alkyl part, in each case optionally substituted in the aryl part once or several times by identical or different substituents, possible substituents in each case being:

Halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, and $R^5$ represents in each case straight-chain or branched alkyl or alkenyl having in each case up to 18 carbon atoms, or represents arylalkyl having 6 to 10 carbon atoms in the aryl part and 1 to 4 carbon atoms in the straight-chain or branched alkyl part, which is optionally substituted in the aryl part once or several times by identical or different substituents, possible substituents being:

Halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, or $R^4$ and $R^5$, together with the nitrogen atom to which they are bonded, represent a saturated five- to seven-membered heterocyclic radical which can optionally contain further heteroatoms—in particular nitrogen, oxygen and/or sulphur—and is optionally substituted once or several times by identical or different substituents, possible substituents being:

Halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms.

Compounds of the formula (I) which can particularly preferably be used are those in which R represents a radical of the formula —S—$R^3$ or —$NR^4R^5$, $R^1$ represents straight-chain or branched alkyl having 1 to 6 carbon atoms, or represents phenyl which is optionally substituted once to three times by identical or different substituents, possible substituents in each case being:

Halogen, cyano, nitro, in each case straight-chain or branched alkyl, alkoxy, alkylthio, alkylsulphinyl or alkylsulphonyl having in each case 1 to 4 carbon atoms and in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, and $R^2$ represents straight-chain or branched alkyl having 1 to 6 carbon atoms, or $R^1$ and $R^2$ together with the nitrogen atom to which they are bonded, represent a saturated five- to seven-membered heterocyclic radical which can optionally contain a further heteroatom—in particular nitrogen, oxygen and/or sulphur—and is optionally substituted once to four times by identical or different substituents, possible substituents being:

Halogen or in each case straight-chain or branched alkyl or alkoxy having in each case 1 to 4 carbon atoms, X represents a halide anion, a phosphate anion, a hexafluorophosphate anion, a sulphate anion, a hydrogensulphate anion, a nitrate anion, a carbonate anion, a perchlorate anion or a tetrafluoroborate anion, and in which $R^3$ represents straight-chain or branched alkyl having 1 to 4 carbon atoms, or represents arylalkyl having 6 or 10 carbon atoms in the aryl part and 1 or 2 carbon atoms in the alkyl part or heteroarylalkyl having 2 to 5 carbon atoms and 1 to 3 identical or different heteroatoms—in particular nitrogen, oxygen and/or sulphur—in the heteroaryl part and 1 or 2 carbon atoms in the alkyl part, in each case optionally substituted in the aryl part once to three times by identical or different substituents, possible substituents in each case being:

Fluorine, chlorine, bromine, iodine, cyano, nitro, carbamoyl, in each case straight-chain or branched alkyl, alkoxy or alkoxycarbonyl having in each case 1 to 3 carbon atoms or in each case straight-chain or branched halogenoalkyl or halogenoalkoxy having in each case 1 to 3 carbon atoms and 1 to 7 identical or different halogen atoms, $R^4$ represents in each case straight-chain or branched alkyl, alkenyl or alkynyl having in each case up to 6 carbon atoms, or represents straight-chain or branched halogenoalkyl having 1 to 4 carbon atoms and 1 to 9 identical or different halogen atoms, or represents in each case straight-chain or branched cyanoalkyl, dioxolanylalkyl, alkoxyalkyl or dialkylaminoalkyl having in each case 1 to 4 carbon atoms in the individual alkyl parts, or represents cyanoalkylalkyl having from 3 to 7 carbon atoms in the cycloalkyl part and 1 to 4 carbon atoms in the straight-chain or branched alkyl part, or represents aryl having 6 or 10 carbon atoms, arylalkyl having 6 or 10 carbon atoms in the aryl part and 1 or 2 carbon atoms in the alkyl part or heteroarylalkyl having 2 to 5 carbon atoms and 1 to 3 identical or different heteroatoms—in particular nitrogen, oxygen and/or sulphur—in the heteroaryl part and 1 or 2 carbon atoms in the alkyl part, in each case optionally substituted in the aryl part once to three times by identical or different substituents, possible substituents in each case being:

Fluorine, chlorine, bromine, iodine, in each case straight-chain or branched alkyl or alkoxy having in each case 1 to 3 carbon atoms or in each case straight-chain or branched halogenoalkyl or halogenoalkoxy having in each case 1 to 3 carbon atoms and 1 to 7 identical or different halogen atoms, and $R^5$ represents in each case straight-chain or branched alkyl or alkenyl having in each case up to 6 carbon atoms, or represents arylalkyl having 6 or 10 carbon atoms in the aryl part and 1 or 2 carbon atoms in the alkyl part, which is optionally substituted in the aryl part once to three times by identical or different substituents, possible substituents being:

Fluorine, chlorine, bromine, iodine, in each case straight-chain or branched alkyl or alkoxy having in each case 1 to 3 carbon atoms or in each case straight-chain or branched halogenoalkyl or halogenoalkoxy having in each case 1 to 3 carbon atoms and 1 to 7 identical or different halogen atoms, or $R^4$ and $R^5$ together with the nitrogen atom to which they are bonded, represent a saturated five- to seven-membered heterocyclic radical which can optionally contain a further heteroatom—in particular nitrogen, oxygen or sulphur—and is optionally substituted once to four times by identical or different substituents, possible substituents being:

Halogen or in each case straight-chain or branched alkyl or alkoxy having in each case 1 to 4 carbon atoms.

Compounds of the formula (I) which can especially preferably be used are those in which R represents a radical of the formula —S—$R^3$ or —$NR^4R^5$, $R^1$ represents straight-chain or branched alkyl having 1 to 4 carbon atoms, or represents phenyl which is optionally substituted once or twice by identical or different substituents, possible substituents in each case being:

Fluorine, chlorine, bromine, cyano, nitro, methyl, ethyl, n- or i-propyl, n-, i-, s- or t-butyl, methoxy, ethoxy, n-or i-propoxy, n-, i-, s-or t-butoxy, trifluoromethyl, difluoromethyl, trifluoromethoxy or difluoromethoxy, and $R^2$ represents straight-chain or branched alkyl having 1 to 4 carbon atoms, or $R^1$ and $R^2$, together with the nitrogen atom to which they are bonded, represent a pyrrolidinyl, piperidinyl, perhydroazepinyl, piperazinyl or morpholinyl radical which is optionally substituted once or twice, possible substituents in each case being:

chlorine, methyl, ethyl, methoxy or ethoxy, and

X represents a fluoride, chloride, bromide, iodide or tetrafluoroborate anion, and wherein X represents methyl or ethyl, or represents phenyl, naphthyl, benzyl or pyridylmethyl, in each case optionally substituted in the aryl part once or twice by identical or different substituents, possible substituents in each case being:

Fluorine, chlorine, bromine, cyano, nitro, methyl, ethyl, n- or i-propyl, methoxy, ethoxy, n- or i-propoxy, methoxycarbonyl, ethoxycarbonyl, carbamoyl, trifluoromethyl, difluoromethyl, trifluoromethoxy or difluoromethoxy, $R^4$ represents methyl, ethyl, n- or i-propyl, n-, i-, s- or t-butyl, allyl, propargyl, cyanethyl, methoxyethyl, ethoxyethyl, dimethylaminoethyl, diethylaminoethyl, dioxolanylmethyl, cyclopropylmethyl or cyclohexylmethyl, or represents phenyl, naphthyl, benzyl, phenylethyl or pyridylmethyl, in each case optionally substituted in the aryl part once or twice by identical or different substituents, possible substituents in each case being:

Fluorine, chlorine, bromine, methyl, ethyl, n- or i-propyl, methoxy, ethoxy, n- or i-propoxy, trifluoromethyl, difluoromethyl, trifluoromethoxy or difluoromethoxy and $R^5$ represents methyl, ethyl, n-or i-propyl, n-, i-, s- or t-butyl or allyl, or represents benzyl which is optionally substituted in the aryl part once or twice by identical or different substituents, possible substituents being:

Fluorine, chlorine, bromine, methyl, ethyl, n- or i- propyl, methoxy, ethoxy, n- or i-propoxy, trifluoromethyl, difluoromethyl, trifluoromethoxy or difluoromethoxy, or $R^4$ and $R^5$, together with the nitrogen atom to which they are bonded, represent a pyrrolidinyl, piperidinyl, perhydroazepinyl, piperazinyl or morpholinyl radical which is optionally substituted once or twice, possible substituents in each case being:

Chlorine, methyl, ethyl, methoxy or ethoxy.

The following 1,2,4-dithiazolium salts of the general formula (I) may be mentioned specifically, in addition to the compounds mentioned in the preparation examples:

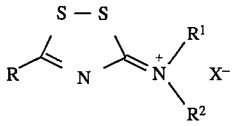

(I)

| R | R¹ | R² | X |
|---|---|---|---|
| 4-Cl-C₆H₄-CH₂-S- | CH₃ | CH₃ | Br⁻ |
| 2,4-Cl₂-C₆H₃-CH₂-S- | CH₃ | CH₃ | Br⁻ |
| 3-Cl-C₆H₄-CH₂-S- | CH₃ | CH₃ | BF₄⁻ |
| 2-F-C₆H₄-CH₂-S- | CH₃ | CH₃ | BF₄⁻ |
| 4-F-C₆H₄-CH₂-S- | CH₃ | CH₃ | BF₄⁻ |
| 2-naphthyl-CH₂-S- | CH₃ | CH₃ | Br⁻ |
| 2,4-F₂-C₆H₃-CH₂-S- | -CH₂-(CH₂)₃-CH₂- | | Br⁻ |
| 4-F₃C-C₆H₄-CH₂-S- | -CH₂-(CH₂)₃-CH₂- | | BF₄⁻ |
| 6-Cl-pyridin-3-yl-CH₂-S- | -CH₂-(CH₂)₃-CH₂- | | BF₄⁻ |
| CH₃-S- | -CH₂-(CH₂)₂-CH₂- | | I⁻ |
| CH₃-S- | C₂H₅ | C₂H₅ | I⁻ |
| C₂H₅-S- | C₂H₅ | C₂H₅ | I⁻ |
| C₆H₅-CH₂-S- | C₂H₅ | C₂H₅ | BF₄⁻ |
| (C₂H₅)₂N- | -CH₂-(CH₂)₃-CH₂- | | I⁻ |
| (n-C₃H₇)₂N- | -CH₂-(CH₂)₃-CH₂- | | I⁻ |
| (i-C₃H₇)₂N- | -CH₂-(CH₂)₃-CH₂- | | I⁻ |
| pyrrolidin-1-yl | -CH₂-(CH₂)₃-CH₂- | | I⁻ |

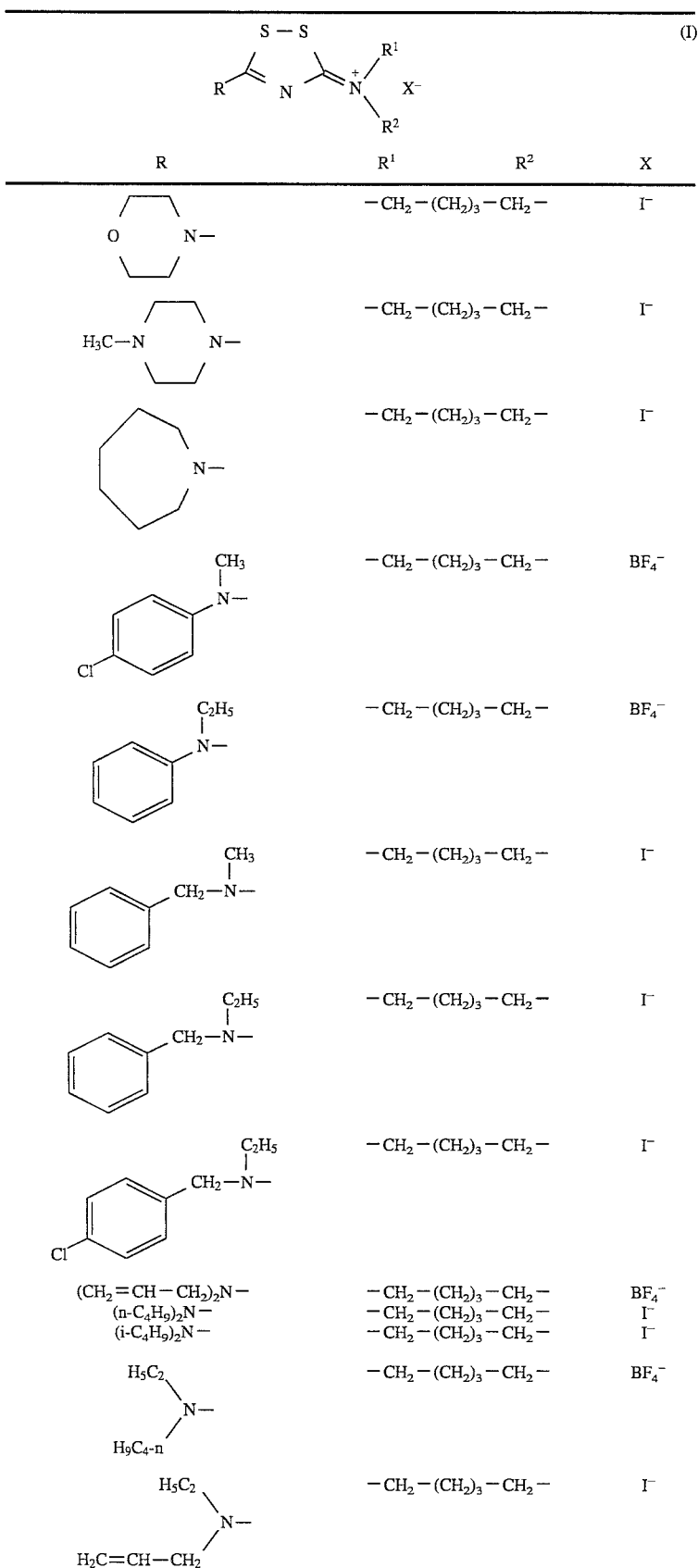

-continued $$\underset{R}{\overset{S-S}{\diagdown}}\underset{N}{\diagdown}\overset{}{=}\underset{N^+}{\overset{R^1}{\diagdown}}\ X^- \quad (I)$$

| R | R¹ | R² | X |
|---|---|---|---|
| 4-CH₃O-C₆H₄-N(CH₃)- | -CH₂-(CH₂)₂-CH₂- | | I⁻ |
| 2-Cl-C₆H₄-N(C₂H₅)- | -CH₂-(CH₂)₂-CH₂- | | BF₄⁻ |
| 2-F-C₆H₄-N(C₂H₅)- | -CH₂-(CH₂)₂-CH₂- | | BF₄⁻ |
| pyrrolidin-1-yl | C₂H₅ | C₂H₅ | I⁻ |
| hexamethyleneimin-1-yl | C₂H₅ | C₂H₅ | BF₄⁻ |
| 4-methylpiperazin-1-yl | C₂H₅ | C₂H₅ | I⁻ |
| morpholin-4-yl | C₂H₅ | C₂H₅ | I⁻ |
| 2,6-dimethylmorpholin-4-yl | C₂H₅ | C₂H₅ | I⁻ |
| C₆H₅-CH₂-N(CH₃)- | C₂H₅ | C₂H₅ | I⁻ |
| C₆H₅-CH₂-N(C₂H₅)- | C₂H₅ | C₂H₅ | I⁻ |
| (C₆H₅-CH₂)₂N- | C₂H₅ | C₂H₅ | I⁻ |

-continued

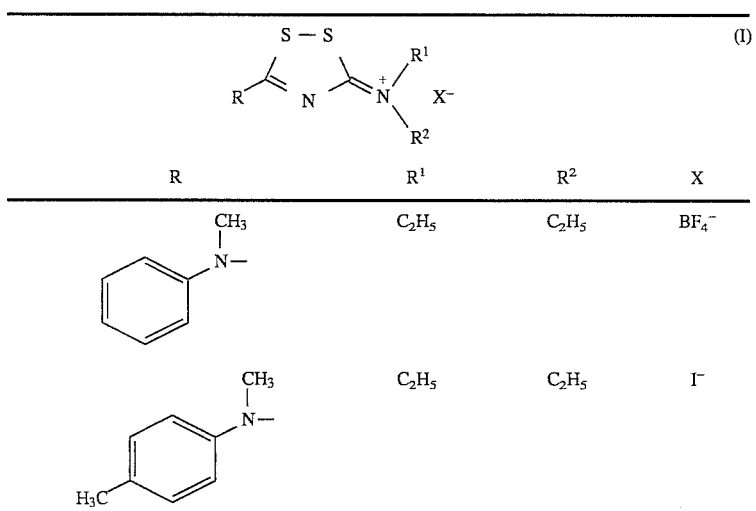

| R | R¹ | R² | X |
|---|---|---|---|
| N-methyl-phenylamino (CH₃, phenyl-N—) | $C_2H_5$ | $C_2H_5$ | $BF_4^-$ |
| N-methyl-4-methylphenylamino | $C_2H_5$ | $C_2H_5$ | $I^-$ |

The 1,2,4-dithiazolium salts of the formula (I) which can be used according to the invention are known in some cases (compare, for example, J. Org. Chem. 36, 3465 [1971]; J. Med. Chem. 15, 315–320 [1972]; J. Econ. Entomol. 65, 390–392 [1972]; Bull. Soc. Chim. Fr. 9–10 Pt. 2, 481–484 [1978]; JP 55081804; JP 57183770; Bull. Chem. Soc. Japan 60, 2686–2688 [1987]; DE 42 27 751).

They are obtained by a process in which 1,2,4-dithiazoline- 5-thiones of the formula (II)

in which

R¹ and R² have the abovementioned meaning, are reacted with alkyl iodides of the formula (III)

in which

R³ has the abovementioned meaning, if appropriate in the presence of a diluent, and, if appropriate, the 1,2,4-dithiazolium salts thus obtainable, of the formula (Ia)

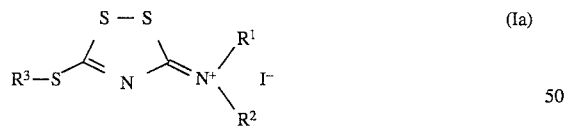

in which

R¹, R² and R³ have the abovementioned meaning, are then reacted in a subsequent second stage with amines of the formula (IV),

in which

R⁴ and R⁵ have the abovementioned meaning, if appropriate in the presence of a diluent, and, if appropriate, the anion is then replaced by reaction with an inorganic acid or a corresponding salt.

If, for example, 3-dimethylamino- 1,2,4-dithiazoline-5-thione, methyl iodide and 2,6-dimethylmorpholine are used as starting substances, the course of the reaction in the preparation process can be represented by the following equation:

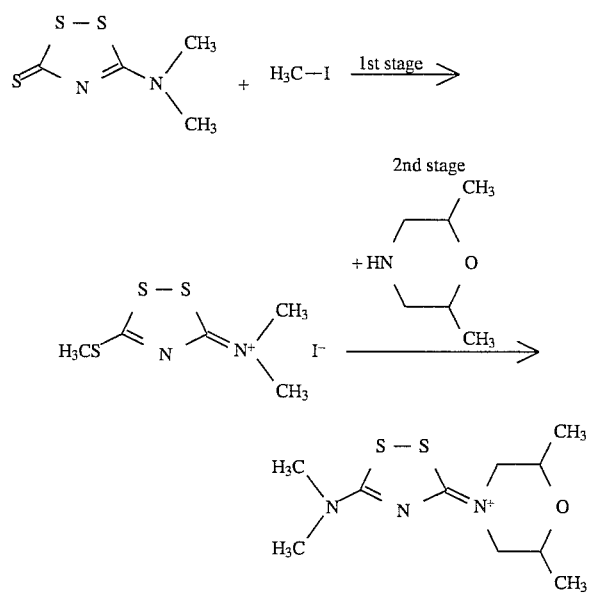

Formula (II) provides a general definition of the 1,2,4-dithiazoline- 5-thiones required as starting substances for carrying out the preparation process. In this formula (II) R¹ and R² preferably represent those radicals which have already been mentioned as preferred for these substituents in connection with the description of the compounds of the formula (I) which can be used according to the invention.

1,2,4-dithiazoline-5-thiones of the formula (II) are known or are obtainable by processes analogous to known processes (compare, for example, J. Amer. Chem. Soc. 80, 414 [1958]; Liebigs Ann. Chem. 285, 174 [1895]).

Formula (III) provides a general definition of the alkyl iodides furthermore required as starting substances for carrying out the preparation process. In this formula (III) R³ preferably represents those radicals which have already been mentioned as preferred for this substituent in connection with the description of the compounds of the formula (I) which can be used according to the invention. Alkyl iodides of the formula (III) are generally known compounds of organic chemistry.

Formula (IV) provides a general definition of the amines furthermore required, if appropriate, as starting substances for carrying out the preparation process. In this formula (IV) $R^4$ and $R^5$ preferably represent those radicals which have already been mentioned as preferred for these substituents in connection with the description of the compounds of the formula (I) which can be used according to the invention. Amines of the formula (IV) are generally known compounds of organic chemistry.

Compounds which are not yet known and to which the invention likewise relates are 1,2,4-dithiazolium salts of the formula (Ib).

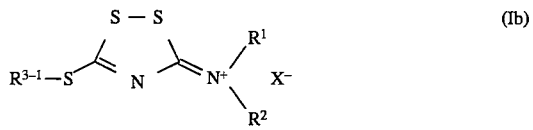

in which $R^1$ represents alkyl or aryl and $R^2$ represents alkyl, or $R^1$ and $R^2$, together with the nitrogen atom to which they are bonded, represent an optionally substituted heterocyclic radical, which can optionally contain further heteroatoms, and X represents the anion of an inorganic acid, and wherein $R^{3-1}$ represents in each case optionally substituted arylalkyl or heterocyclylalkyl.

Possible diluents for carrying out the 1st and 2nd stage of the preparation process are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric acid triamide; esters, such as methyl acetate or ethyl acetate, or sulphoxides, such as dimethyl sulphoxide, or sulphones, such as sulpholane.

The reaction temperatures can be varied within a substantial range in carrying out the 1st stage of the preparation process. The reaction is in general carried out at temperatures between 0° C. and 140° C., preferably at temperatures between 20° C. and 120° C.

The reaction temperatures can be varied within a substantial range in carrying out the 2nd stage of the preparation process. The reaction is in general carried out at temperatures between 0° C. and 140° C., preferably at temperatures between 20° C. and 80° C.

The 1st and the 2nd stage of the preparation process are usually carried out under normal pressure. However, it is also possible to carry out these stages under increased or reduced pressure.

For carrying out the 1st stage of the preparation process, in general 1.0 to 1.5 mol, preferably 1.0 to 1.1 mol, of alkyl iodide of the formula (III) are employed per mol of 1,2,4-dithiazoline-5-thione of the formula (II). The reaction is carried out and the reaction products are worked up and isolated by customary processes (in this context, compare also the preparation examples).

For carrying out the 2nd stage of the preparation process, in general 1.0 to 1.5 mol, preferably 1.0 to 1.1 mol, of amine of the formula (IV) are employed per mol of 1,2,4-dithiazoliumiodide of the formula (Ia). The reaction is carried out and the reaction products are worked up and isolated by customary processes (in this context, compare also the preparation examples).

The end products of the formula (I) are likewise purified with the aid of customary processes, for example by column chromatography or by recrystallization.

The products are characterized with the aid of the melting point or, in the case of compounds which do not crystallize, with the aid of proton nuclear magnetic resonance spectroscopy ($^1$H-NMR).

Substances from the class of dithiazolium salts are described in their protective action by way of example in the following: in vitro in the TNF-α-mediated cytotoxicity test, and in vivo on mice which have been exposed to an endotoxin shock.

The TNF-α-mediated cytotoxicity test was carried out using the cell line WEHI-164-clone-13, a fibrosarcoma line, essentially in accordance with the working instructions of Espevik and Nissen-Meyer 1986 (J. Immunol. Methods 95: 99–105). For this, $2.5 \times 10^4$ cells per depression of a 96-well microtiter plate were subjected to preincubation for 5 hours using RPMI 1640 and 5% foetal calf serum. When the time had expired, various substance amounts of a dithiazolium salt (3-10-30-100 µg/ml), actinomycin (4 µg/ml) and TNF-α (25 µg/ml) were added to the cells and subjected to further incubation for 18 hours.

Vitality determinations were carried out with the aid of a colorimetric method using 3-[4,5-dimethylthiazol-2-yl]-2,5-diphenyltetrazolium bromide (MTT) in a microtiterplate evaluation system at a wavelength of 570 nm and a reference wavelength of 630 mm (in accordance with Mosmann, 1983, J. Immunol. Methods 65: 55).

In vivo experiments on inhibition of provoked endotoxin shock were carried out on female inbred mice ($F_1$[B6D2]). Endotoxin/lipopolysaccharide (LPS) from Salmonella abortus equi (0.1 µg/mouse) was administered intraperitoneally or intravenously in association with D-galactosamine hydrochloride (D-GalN; 60 mg/kg of bodyweight) in accordance with reports by Galanos et al. (1979, Proc. Natl. Acad. Sci. USA 76: 5939; V. Lehmann et al. 1987, J. Exp. Med. 165: 657). The substances were administered intraperitoneally one hour before inducement of the endotoxemic shock. The observation period was 48 hours.

TABLE 1

Influence of dithiazolium salts on the course of endotoxemic shock in D-GalN-sensitized mice and on the TNF-α-mediated cytotoxicity of cells with the cell line WEHI 164-clone 13.

| Substance Example | in-vivo | | | | | in-vitro[1] |
|---|---|---|---|---|---|---|
| | LPS + D-GalN [Control] | Substance[2] + D-GalN [Control] | Dose (mg/kg) | | | |
| | | | 10 | 30 | 60 | |
| | | | lethality | | | |
| 10 | 100 | 0 | 20 | 0 | 0 | + |
| 5 | 100 | 0 | 40 | 0 | 0 | + |
| 3 | 100 | 0 | 80 | 40 | 0 | +/– |
| 8 | 100 | 0 | 40 | 0 | 0 | +/– |
| 2 | 100 | 0 | 100 | 20 | 0 | + |
| 43 | 100 | 0 | 20 | 20 | 0 | n.d.[3] |
| 46 | 100 | 0 | 0 | 0 | 0 | n.d. |
| 48 | 100 | 0 | 0 | 0 | 0 | n.d. |

[1] Inhibition of TNF-α-mediated lyses of the target cells

TABLE 1-continued

Influence of dithiazolium salts on the course of endotoxemic shock in D-GalN-sensitized mice and on the TNF-α-mediated cytotoxicity of cells with the cell line WEHI 164-clone 13.

| Sub-stance Example | in-vivo | | | | | in-vitro[1] |
|---|---|---|---|---|---|---|
| | LPS + D-GalN [Control] | Substance[2] + D-GalN [Control] | Dose (mg/kg) | | | |
| | | | 10 | 30 | 60 | |
| | | | lethality | | | |

[2] 60 mg/kg
[3] not carried out

The protective properties moreover can be based, for example, on an inhibition of TNF-α/β or/and IL-1α/β synthesis, on a TNF-α/β or/and IL-1α/β receptor blockade, on an inhibition of leucocyte adherence to the endothelium or else on other mechanisms.

PREPARATION EXAMPLES

EXAMPLE 1

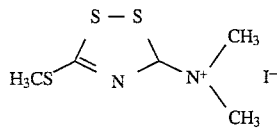

44.5 g (0.252 mol) of 3-dimethylamino-1,2,4-dithiazoline-5-thione and 39.1 g (0.275 mol) of methyl iodide in 350 ml of acetonitrile are heated at the reflux temperature for 5 hours. For working up, the reaction mixture is cooled and the crystals which are precipitated are filtered off with suction and dried.

71.8 g (90% of theory) of 3-dimethylamino-5-methylthio-1,2,4-dithiazolium iodide of melting point 161° C. (decomposition) are obtained.

EXAMPLE 2

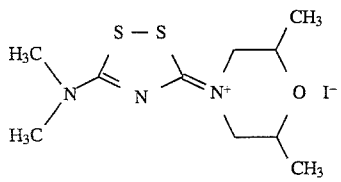

6.4 g (0.02 mol) of 3-dimethylamino-5-methylthio-1,2,4-dithiazoliumiodide and 2.3 g (0.02 mol) of 2,6-dimethyl-morpholine in 50 ml of methylene chloride are heated at reflux temperature for 16 hours. For working up, the cooled reaction mixture is concentrated in vacuo, the residue is stirred with hot ethyl acetate and the mixture is cooled. The crystals which have precipitated are filtered off with suction and dried.

6.7 g (87% of theory) of 4-(5-dimethylamino-3H-1,2,4-dithiazole- 3-ylidene)-2,6-dimethyl-morpholinium iodide of melting point 192° C. (decomposition) are obtained.

EXAMPLE 3

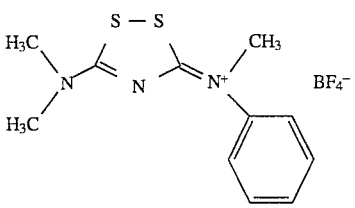

6.4 g (0.02 mol) of 3-dimethylamino-5-methylthio-1,2,4-dithiazolium iodide and 2.1 g (0.02 mol) of N-methylniline in 50 ml of chloroform are heated at reflux temperature for 36 hours. For working up, the cooled reaction mixture is concentrated in vacuo, the residue is taken up in methylene chloride, the mixture is stirred with an saturated aqueous solution of sodium tetrafluoroborate and the organic phase is separated off, washed twice with water, dried over sodium sulphate and concentrated in vacuo.

5.5 g (81% of theory) of N-(5-dimethylamino-3H-1,2,4-dithiazole- 3-ylidene)-N-methylanilinium tetrafluoroborate of melting point 128° C. (decomposition) are obtained.

The following 1,2,4-dithiazolium salts of the general formula (I) are obtained in a corresponding manner and in accordance with the general preparation information:

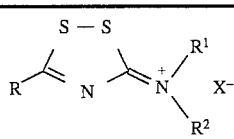
(I)

| Ex. No. | R | $R^1$ | $R^2$ | X | Physical properties |
|---|---|---|---|---|---|
| 4 | —N(CH$_3$)$_2$ | | —CH$_2$—(CH$_2$)$_3$—CH$_2$— | I⁻ | m.p. 87° C. (dec.) |
| 5 | —N(CH$_3$)$_2$ | | —(CH$_2$)$_2$—O—(CH$_2$)$_2$— | I⁻ | ¹H-NMR*): 3,3; 3,45 (d, 6H) |
| 6 | —N(CH$_3$)$_2$ | n-C$_3$H$_7$ | n-C$_3$H$_7$ | I⁻ | m.p. 111–113° C. (dec.) |
| 7 | —N(CH$_3$)$_2$ | | —CH$_2$—(CH$_2$)$_2$—CH$_2$— | I⁻ | m.p. 89° C. (dec.) |

-continued

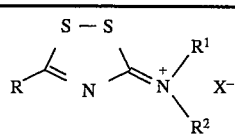
(I)

| Ex. No. | R | R¹ | R² | X | Physical properties |
|---|---|---|---|---|---|
| 8 | $-N(CH_3)_2$ | $-(CH_2)_2-N(CH_3)-(CH_2)_2-$ | | $I^-$ | m.p. 169° C. (dec) |
| 9 | $-N(CH_3)_2$ | $C_2H_5$ | $C_2H_5$ | $I^-$ | m.p. 127° C. (dec.) |
| 10 | $-N(CH_3)_2$ | $i-C_3H_7$ | $i-C_3H_7$ | $I^-$ | m.p. 132° C. (dec.) |
| 11 | $-N(CH_3)_2$ | $n-C_4H_9$ | $n-C_4H_9$ | $I^-$ | ¹H-NMR*): 3,25; 3,4 (d, 6H) |
| 12 | $-N(CH_3)_2$ | $i-C_4H_9$ | $i-C_4H_9$ | $I^-$ | m.p. 99–102° C. (dec.) |
| 13 | 6-chloro-3-pyridyl-$CH_2-S-$ | $CH_3$ | $CH_3$ | $BF_4^-$ | ¹H-NMR*): 3,25; 3,35 (d, 6H) |
| 14 | 1-naphthyl-$CH_2-S-$ | $CH_3$ | $CH_3$ | $BF_4^-$ | m.p. 152° C. |
| 15 | 4-$F_3C$-phenyl-$CH_2-S-$ | $CH_3$ | $CH_3$ | $BF_4^-$ | m.p. 129° C. |
| 16 | 2,4-difluorophenyl-$CH_2-S-$ | $CH_3$ | $CH_3$ | $BF_4^-$ | m.p. 106–108° C. |
| 17 | $-N(CH_3)_2$ | $-CH_2-(CH_2)_4-CH_2-$ | | $BF_4^-$ | ¹H-NMR*): 3,25; 3,4 (d, 6H) |
| 18 | $-N(CH_3)_2$ | $C_2H_5$ | $n-C_4H_9$ | $I^-$ | m.p. 88–92° C. (dec.) |
| 19 | $-N(CH_3)_2$ | $-CH_2-CH=CH_2$ | $-CH_2-CH=CH_2$ | $I^-$ | ¹H-NMR*): 3,3; 3,45 (d, 6H) |
| 20 | $-N(CH_3)_2$ | $-CH_2-C_6H_5$ | $-CH_2-C_6H_5$ | $I^-$ | m.p. 171–174° C. (dec.) |
| 21 | $-N(CH_3)_2$ | $C_2H_5$ | $-CH_2-C_6H_5$ | $I^-$ | ¹H-NMR*): 3,3; 3,45 (d, 6H) |
| 22 | $-N(CH_3)_2$ | $n-C_4H_9$ | $-CH_2-C_6H_5$ | $I^-$ | ¹H-NMR*): 3,3; 3,45 (d, 6H) |
| 23 | $-N(CH_3)_2$ | $n-C_4H_9$ | $-CH_2-C_6H_5$ | $BF_4^-$ | ¹H-NMR*): 3,3; 3,45 (d, 6H) |
| 24 | $-N(CH_3)_2$ | $CH_3$ | $-CH_2-C_6H_5$ | $I^-$ | m.p. 118–121° C. (dec.) |
| 25 | $-N(CH_3)_2$ | $CH_3$ | $C_2H_5$ | $I^-$ | m.p. 82–85° C. (dec.) |
| 26 | $-N(CH_3)_2$ | $CH_3$ | $n-C_3H_7$ | $I^-$ | m.p. 103–105° C. (dec.) |
| 27 | $-N(CH_3)_2$ | $n-C_3H_7$ | $n-C_3H_7$ | $BF_4^-$ | m.p. 102–106° C. |
| 28 | $-N(CH_3)_2$ | $-CH_2-C_6H_5$ | $-CH_2-CH_2-C_6H_5$ | $I^-$ | m.p. 119–121° C. (dec.) |
| 29 | $-N(CH_3)_2$ | $CH_3$ | $-CH_2-$(1,3-dioxolan-2-yl) | $I^-$ | m.p. 91–94° C. (dec.) |
| 30 | $-N(CH_3)_2$ | $CH_3$ | $n-C_6H_{13}$ | $I^-$ | m.p. 108–111° C. (dec.) |
| 31 | $-N(CH_3)_2$ | $CH_3$ | $-CH_2-CH_2-CN$ | $I^-$ | m.p. 126° C. (dec.) |
| 32 | $-N(CH_3)_2$ | $-CH_2-C_6H_5$ | $-(CH_2)_2-N(CH_3)_2$ | $BF_4^-$ | ¹H-NMR*): 3,25; 3,4 (d, 6H) |
| 33 | $-N(CH_3)_2$ | $C_2H_5$ | $-(CH_2)_2-N(CH_3)_2$ | $BF_4^-$ | ¹H-NMR*): 3,25; 3,4 (d, 6H) |
| 34 | $-N(CH_3)_2$ | $i-C_3H_7$ | $-CH_2-C_6H_5$ | $I^-$ | m.p. 112–116° C. |
| 35 | $-SCH_3$ | $-CH_2-(CH_2)_3-CH_2-$ | | $I^-$ | ¹H-NMR*): 2,65 (s, 3H) |

-continued

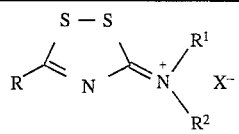

| Ex. No. | R | R¹ | R² | X | Physical properties |
|---|---|---|---|---|---|
| 36 | —N(CH₃)₂ | CH₃ | i-C₃H₇ | I⁻ | m.p. 99–103° C. (dec.) |
| 37 | —N(CH₃)₂ | C₂H₅ | i-C₃H₇ | I⁻ | ¹H-NMR*⁾: 3,25; 3,4 (d, 6H) |
| 38 | —N(CH₃)₂ | CH₃ | t-C₄H₉ | I⁻ | m.p. 96° C. (dec.) |
| 39 | —N(CH₃)₂ | CH₃ | n-C₅H₁₁ | I⁻ | ¹H-NMR*⁾: 3,25; 3,4 (d, 6H) |
| 40 | —N(CH₃)₂ | n-C₃H₇ | —CH₂-cyclopropyl | I⁻ | ¹H-NMR*⁾: 3,25; 3,4 (d, 6H) |
| 41 | —N(CH₃)₂ | C₂H₅ | n-C₃H₇ | I⁻ | ¹H-NMR*⁾: 3,25; 3,4 (d, 6H) |
| 42 | —N(CH₃)₂ | n-C₃H₇ | —CH₂—C₆H₅ | I⁻ | m.p. 103–108° C. (dec.) |
| 43 | —N(CH₃)₂ | CH₃ | —CH₂-(3,4-diCl-C₆H₃) | I⁻ | m.p. 103–108° C. (dec.) |
| 44 | —N(CH₃)₂ | CH₃ | —CH₂-(2-Cl-C₆H₄) | I⁻ | m.p. 116° C. (dec.) |
| 45 | —N(CH₃)₂ | CH₃ | i-C₄H₉ | I⁻ | ¹H-NMR*⁾: 3,4 (s, 6H) |
| 46 | —N(CH₃)₂ | CH₃ | —CH₂-(4-Cl-C₆H₄) | I⁻ | m.p. 112° C. (dec.) |
| 47 | —N(CH₃)₂ | CH₃ | n-C₁₂H₂₅ | I⁻ | m.p. 103–109° C. (dec.) |
| 48 | —N(CH₃)₂ | CH₃ | —CH₂-(2,4-diCl-C₆H₃) | I⁻ | m.p. 127° C. (dec.) |
| 49 | —N(CH₃)₂ | C₂H₅ | —CH₂-(3,4-diCl-C₆H₃) | BF₄⁻ | ¹H-NMR*⁾: 3,25; 3,3 (d, 6H) |
| 50 | —N(CH₃)₂ | C₂H₅ | —CH₂-(2-Cl-C₆H₄) | I⁻ | m.p. 97–101° C. (dec.) |
| 51 | —N(CH₃)₂ | C₂H₅ | —CH₂-(2,4-diCl-C₆H₃) | I⁻ | m.p. 133° C. (dec.) |
| 52 | —N(CH₃)₂ | C₂H₅ | —CH₂-(4-Cl-C₆H₄) | I⁻ | m.p. 96–101° C. (dec.) |

-continued

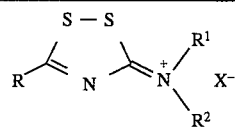
(I)

| Ex. No. | R | R¹ | R² | X | Physical properties |
|---|---|---|---|---|---|
| 53 | $-N(CH_3)_2$ | $C_2H_5$ | $-CH_2-$(2-F-C₆H₄) | $I^-$ | m.p. 85–88° C. (dec.) |
| 54 | $-N(CH_3)_2$ | $C_2H_5$ | $-CH_2-$(2-CH₃-C₆H₄) | $I^-$ | m.p. 104–109° C. (dec.) |
| 55 | $-N(CH_3)_2$ | $C_2H_5$ | $-CH_2-$(4-CH₃-C₆H₄) | $I^-$ | m.p. 106–111° C. (dec.) |
| 56 | $-N(CH_3)_2$ | $t-C_4H_9$ | $-CH_2-C_6H_5$ | $I^-$ | m.p. 112° C. (dec.) |
| 57 | $-N(CH_3)_2$ | $C_2H_5$ | $-CH_2-CH=CH_2$ | I | m.p. 167° C. (dec.) |
| 58 | $-N(CH_3)_2$ | $CH_3$ | 4-Cl-C₆H₄ | I | m.p. 138° C. (dec.) |
| 59 | $-N(CH_3)_2$ | $CH_3$ | C₆H₅ | I | m.p. 144–147° C. (dec.) |
| 60 | $-N(CH_3)_2$ | $CH_3$ | 4-OCH₃-C₆H₄ | I | m.p. 173° C. (dec.) |
| 61 | $-N(CH_3)_2$ | $-CH_2-CH=CH_2$ | C₆H₅ | I | ¹H-NMR δ=3.25; 3.4 (d, 6H) |
| 62 | $-N(CH_3)_2$ | $C_2H_5$ | C₆H₅ | I | m.p. 131–136° C. (dec.) |
| 63 | $-N(CH_3)_2$ | $-CH_2CH_2CN$ | C₆H₅ | I | m.p 178° C. (dec.) |
| 64 | $-N(CH_3)_2$ | $-CH_2-C_6H_5$ | C₆H₅ | I | m.p. 66° C. (dec.) |
| 65 | $-N(CH_3)_2$ | $-CH(CH_3)_2$ | 2-NC-5-CH₃-C₆H₃ | I | ¹H-NMR δ=3.25; 3.35 (d, 6H) |
| 66 | $-N(CH_3)_2$ | $n-C_4H_9$ | C₆H₅ | I | ¹H-NMR δ=3.3; 3,45 (d, 6H) |

-continued

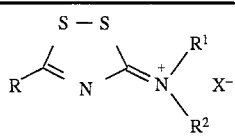
(I)

| Ex. No. | R | R¹ | R² | X | Physical properties |
|---|---|---|---|---|---|
| 67 | —N(CH₃)₂ | C₂H₅ | 2-NO₂-phenyl | I | m.p. 112–116°C. (dec.) |
| 68 | —N(CH₃)₂ | CH₃ | 4-NO₂-phenyl | I | m.p. 174–177° C. (dec.) |
| 69 | —N(CH₃)₂ | CH₃ | 2-(H₂N—C(O))-phenyl | I | m.p. 141–145° C. (dec.) |
| 70 | —N(CH₃)₂ | CH₃ | 2,4-difluorophenyl | I | m.p. 192–195° C. (dec.) |
| 71 | —N(CH₃)₂ | CH₃ | 2-NO₂-phenyl | I | m.p. 119–125° C. (dec.) |
| 72 | —N(CH₃)₂ | CH₃ | 3,4-dichlorophenyl | I | m.p. 128° C. (dec.) |
| 73 | —N(CH₃)₂ | CH₃ | 4-OCF₃-phenyl | I | ¹H-NMR δ = 3.3; 3.5 (d, 6H) |
| 74 | —N(CH₃)₂ | CH₃ | 2-Cl-phenyl | I | m.p. 189° C. (dec.) |
| 75 | —N(CH₃)₂ | CH₃ | 2-CF₃-phenyl | I | m.p. 134–138° C. (dec.) |
| 76 | —N(CH₃)₂ | C₂H₅ | 2,3,6-trimethylphenyl | I | m.p. 189° C. (dec.) |
| 77 | —N(CH₃)₂ | CH₃ | CH₃ | I | m.p. 231° C. |

-continued

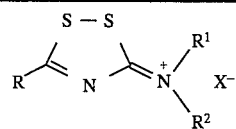

(I)

| Ex. No. | R | R¹ | R² | X | Physical properties |
|---|---|---|---|---|---|
| | | | | | (dec.) |
| 78 | —N(CH₃)₂ | CH₂CH₂NEt₂ | ⌬ (phenyl) | I | ¹H-NMR δ = 3.3; 3.45 (d, 6H) |
| 79 | C₂H₅S— | CH₃ | CH₃ | I | m.p. 53–59° C. |
| 80 | nC₃H₇S— | CH₃ | CH₃ | I | m.p. 123–127° C. |
| 81 | iC₃H₇S— | CH₃ | CH₃ | I | m.p. 141–144° C. |
| 82 | nC₄H₉S— | CH₃ | CH₃ | I | m.p. 99–101° C. |
| 83 | —N(CH₃)₂ | cyclohexyl | phenyl | I | m.p. 179° C. (dec.) |
| 84 | —N(CH₃)₂ | CH₂CH₂NMe₂ | phenyl | I | ¹H-NMR δ = 3.35; 3.45 (d, 6H) |
| 85 | —N(CH₃)₂ | CH₃ | 4-CH₃-phenyl | I | m.p. 135° C. (dec.) |
| 86 | —N(CH₃)₂ | nC₃H₇ | phenyl | I | ¹H-NMR δ = 3.3; 3.4 (d, 6H) |
| 87 | —N(CH₃)₂ | iC₃H₇ | 4-(phenylamino)phenyl | I | m.p. 86° C. (dec.) |
| 88 | —N(CH₃)₂ | C₂H₅ | 2-CH₃-phenyl | I | m.p. 93° C. (dec.) |
| 89 | (CH₃)₂CHCH₂S— | CH₃ | CH₃ | I | m.p. 119–123° C. (dec.) |
| 90 | (CH₃)₃C—S— | CH₃ | CH₃ | I | m.p. 167° C. (dec.) |
| 91 | (C₂H₅)(CH₃)CH—S— | CH₃ | CH₃ | I | m.p. 91–96° C. (dec.) |
| 92 | nC₅H₁₁S— | CH₃ | CH₃ | I | m.p. 128–132° C. |
| 93 | (CH₃)₂CHCH₂CH₂S— | CH₃ | CH₃ | I | m.p. 128–132° C. |
| 94 | nC₄F₉S— | CH₃ | CH₃ | I | m.p. 198–201° C. |
| 95 | —N(CH₃)₂ | \multicolumn{2}{c}{—N(piperazine)N—C₂H₅} | I | m.p. 177° C. (dec.) |
| 96 | —N(CH₃)₂ | \multicolumn{2}{c}{—N(piperazine)N—CH₂-cyclohexyl} | I | m.p. 229° C. (dec.) |

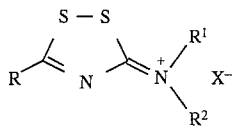

| Ex. No. | R | R¹ | R² | X | Physical properties |
|---------|---|----|----|---|---------------------|

*)The $^1$H-NMR spectra were recorded in hexadeutero-dimethyl sulphoxide (DMSO-$d_6$) with tetramethylsilane (TMS) as the internal standard. The chemical shift as the δ value in ppm is stated.

We claim:

1. A method of inhibiting TNF-α in a patient in need thereof which comprises administering to such patient an amount effective therefor of a 1,2,4-dithiazolium salt of the formula

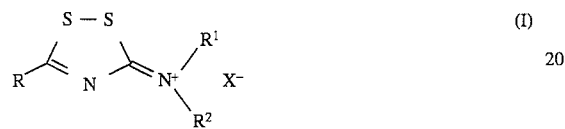

in which

R represents a radical of the formula —S—$R^3$ or —$NR^4R^5$, $R^1$ represents straight-chain or branched alkyl having 1 to 8 carbon atoms, or represents aryl having 6 to 10 carbon atoms which is optionally substituted once or several times by identical or different substituents, wherein the substituents are:

halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl parts and phenyl which is optionally substituted once or several times by identical or different substituents wherein the substituents are halogen and/or straight-chain or branched alkyl and/or straight-chain or branched alkoxy and/or straight-chain or branched halogenoalkyl and/or straight-chain or branched halogenoalkoxy having in each case 1 to 4 carbon atoms and, optionally, 1 to 9 identical or different halogen atoms, and $R^2$ represents straight-chain or branched alkyl having 1 to 8 carbon atoms, or $R^1$ and $R^2$, together with the nitrogen atom to which they are bonded, represent a saturated five- to seven-membered heterocyclic radical which is optionally substituted once or several times by identical or different substituents and optionally contains further heteroatoms wherein the heteroatoms are selected from the group consisting of nitrogen, oxygen and sulphur and the substituents are:

halogen, in each case straight-chain or branched alkyl or alkoxy having in each case 1 to 4 carbon atoms or in each case straight-chain or branched halogenoalkyl or halogeno alkoxy having in each case 1 to 4 carbon atoms and 1 to 9 identical or different halogen atoms, and X represents the anion of an inorganic acid, and wherein $R^3$ represents straight-chain or branched alkyl having 1 to 8 carbon atoms, or represents arylalkyl having 6 to 10 carbon atoms in the aryl part and 1 to 4 carbon atoms in the straight-chain or branched alkyl part or heteroarylalkyl having 2 to 9 carbon atoms and 1 to 3 identical or different heteroatoms wherein the heteroatoms are nitrogen, oxygen and sulphur in the heteroaryl part and 1 to 4 carbon atoms in the straight-chain or branched alkyl part, in each case optionally substituted in the aryl or hetaryl part once or several times by identical or different substituents, wherein the substituents are:

halogen, cyano, nitro, carbamoyl, in each case straight-chain or branched alkyl, alkoxy or alkoxycarbonyl having in each case 1 to 4 carbon atoms or in each case straight-chain or branched halogenoalkyl or halogenoalkoxy having in each case 1 to 4 carbon atoms and 1 to 9 identical different halogen atoms, $R^4$ represents in each case straight-chain or branched alkyl, alkenyl or alkynyl having each case up to 8 carbon atoms, or represents straight-chain or branched halogenoalkyl having 1 to 8 carbon atoms and 1 to 17 identical or different halogen atoms, or represents in each case straight-chain or branched cyanoalkyl, dioxolanylalkyl, alkoxyalkyl or dialkylaminoalkyl having in each case 1 to 8 carbon atoms in the individual alkyl parts, or represents cycloalkylalkyl having from 3 to 8 carbon atoms in the cycloalkyl part and 1 to 8 carbon atoms in the straight-chain or branched alkyl part, or represents aryl having 6 to 10 carbon atoms, arylalkyl having 6 to 10 carbon atoms in the aryl part and 1 to 4 carbon atoms in the straight-chain or branched alkyl part or heteroarylalkyl having 2 to 9 carbon atoms and 1 to 3 identical or different heteroatoms wherein the heteroatoms are nitrogen, oxygen and sulphur in the heteroaryl part and 1 to 4 carbon atoms in the straight-chain or branched alkyl part, in each case optionally substituted in the aryl or heteroaryl part once or several times by identical or different substituents, wherein the substituents are:

halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, and $R^5$ represents in each case straight-chain or branched alkyl or alkenyl having in each case up to 8 carbon atoms, or represents arylalkyl having 6 to 10 carbon atoms in the aryl part and 1 to 4 carbon atoms in the straight-chain or branched alkyl part, which is optionally substituted in the aryl part once or several times by identical or different substituents, wherein the substituents are:

halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, or $R^4$ and $R^5$, together with the nitrogen atom to which they are bonded, represent a saturated five-to seven-membered heterocyclic radical which can optionally contain further heteroatoms wherein said heteroatoms are nitrogen, oxygen and/or sulphur and which is optionally substituted once or several times by identical or different substituents, wherein the substituents are:

halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms.

2. The method according to claim 1, in which

R represents a radical of the formula —S—$R^3$ or —$NR^4R^5$, $R^1$ represents straight-chain or branched alkyl having 1 to 6 carbon atoms, or represents phenyl which is optionally substituted once to three times by identical or different substituents, wherein the substituents are:

halogen, cyano, nitro, in each case straight-chain or branched alkyl, alkoxy, alkylthio, alkylsulphinyl or alkylsulphonyl having in each case 1 to 4 carbon atoms and in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, and $R^2$ represents straight-chain or branched alkyl having 1 to 6 carbon atoms, or $R^1$ and $R^2$, together with the nitrogen atom to which they are bonded, represent a saturated five- to seven-membered heterocyclic radical which optionally contains a further heteroatom selected from the group consisting of nitrogen, oxygen and sulphur and which is optionally substituted once to four times by identical or different substituents, wherein the substituents are:

halogen or in each case straight-chain or branched alkyl or alkoxy having in each case 1 to 4 carbon atoms, X represents a halide anion, a phosphate anion, a hexafluorophosphate anion, a sulphate anion, a hydrogensulphate anion, a nitrate anion, a carbonate anion, a perchlorate anion or a tetrafluoroborate anion, and in which $R^3$ represents straight-chain or branched alkyl having 1 to 4 carbon atoms, or represents arylalkyl having 6 or 10 carbon atoms in the aryl part and 1 or 2 carbon atoms in the alkyl part or heteroarylalkyl having 2 to 5 carbon atoms and 1 to 3 identical or different heteroatoms wherein the heteroatoms are nitrogen, oxygen and sulphur in the heteroaryl part and 1 to 2 carbon atoms in the alkyl part, in each case optionally substituted in the aryl or heteroaryl part once to three times by identical or different substituents, wherein the substituents are:

fluorine, chlorine, bromine, iodine, cyano, nitro, carbamoyl, in each case straight-chain or branched alkyl, alkoxy or alkoxycarbonyl having in each case 1 to 3 carbon atoms or in each case straight-chain or branched halogenoalkyl or halogenoalkoxy having in each case 1 to 3 carbon atoms and 1 to 7 identical or different halogen atoms, $R^4$ represents in each case straight-chain or branched alkyl, alkenyl or alkynyl having in each case up to 6 carbon atoms, or represents straight-chain or branched halogenoalkyl having 1 to 4 carbon atoms and 1 to 9 identical or different halogen atoms, or represents in each case straight-chain or branched cyanoalkyl, dioxolanylalkyl, alkoxyalkyl or dialkylaminoalkyl having in each case 1 to 4 carbon atoms in the individual alkyl parts, or represents cyanoalkylalkyl having from 3 to 7 carbon atoms in the cycloalkyl part and 1 to 4 carbon atoms in the straight-chain or branched alkyl part, or represents aryl having 6 or 10 carbon atoms, arylalkyl having 6 or 10 carbon atoms in the aryl part and 1 or 2 carbon atoms in the alkyl part or heteroarylalkyl having 2 to 5 carbon atoms and 1 to 3 identical or different heteroatoms wherein the heteroatoms are nitrogen, oxygen and sulphur in the heteroaryl part and 1 or 2 carbon atoms in the alkyl part, in each case optionally substituted in the aryl part once to three times by identical or different substituents, wherein the substituents are:

fluorine, chlorine, bromine, iodine, in each case straight-chain or branched alkyl or alkoxy having in each case 1 to 3 carbon atoms or in each case straight-chain or branched halogenoalkyl or halogenoalkoxy having in each case 1 to 3 carbon atoms and 1 to 7 identical or different halogen atoms, and $R^5$ represents in each case straight-chain or branched alkyl or alkenyl having in each case up to 6 carbon atoms, or represents arylalkyl having 6 to 10 carbon atoms in the aryl part and 1 or 2 carbon atoms in the alkyl part, which is optionally substituted in the aryl part once to three times by identical or different substituents, wherein the substituents are:

fluorine, chlorine, bromine, iodine, in each case straight-chain or branched alkyl or alkoxy having in each case 1 to 3 carbon atoms or in each case straight-chain or branched halogenalkyl or halogenoalkoxy having in each case 1 to 3 carbon atoms and 1 to 7 identical or different halogen atoms, or $R^4$ and $R^5$, together with the nitrogen atom to which they are bonded, represent a saturated five- to seven-membered heterocyclic radical which can optionally contain a further heteroatom selected from the group consisting of nitrogen, oxygen and sulphur and which is optionally substituted once to four times by identical or different substituents, wherein the substituents are:

halogen or in each case straight-chain or branched alkyl or alkoxy having in each case 1 to 4 carbon atoms.

3. The method according to claim 1, in which

R represents a radical of the formula —S—$R^3$ or —$NR^4R^5$, $R^1$ represents straight-chain or branched alkyl having 1 to 4 carbon atoms, or represents phenyl which is optionally substituted once or twice by identical or different substituents, wherein the substituents are:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, tri fluoromethyl, difluoromethyl, trifluoromethoxy or difluoromethoxy, and $R^2$ represents straight-chain or branched alkyl having 1 to 4 carbon atoms, or $R^1$ and $R^2$, together with the nitrogen atom to which they are bonded, represent a pyrrolidinyl, piperidinyl, perhydroazepinyl, piperazinyl or morpholinyl radical which is optionally substituted once or twice, wherein the substituents are:
chlorine, methyl, ethyl, methoxy or ethoxy, and X represents a fluoride, chloride, bromide, iodide or tetrafluoroborate anion, and wherein $R^3$ represents methyl or ethyl, or represents phenyl, naphthyl, benzyl or pyridylmethyl, in each case optionally substituted in the aryl or heteroaryl part once or twice by identical or different substituents, wherein the substituents are:
fluorine, chlorine, bromine, cyano, nitro, methyl, ethyl, n- or i-propyl, methoxy, ethoxy, n- or i-propoxy, methoxycarbonyl, ethoxycarbonyl, carbamoyl, trifluoromethyl, difluoromethyl, trifluoromethoxy or difluoromethoxy, $R^4$ represents methyl, ethyl, n- or i-propyl, n-, i-, s- or t-butyl, allyl, propargyl, cyanethyl, methoxyethyl, ethoxyethyl, dimethylaminoethyl, diethylaminoethyl, dioxolanylmethyl, cyclopropylmethyl or cyclohexylmethyl, or represents phenyl, naphthyl, benzyl, phenylethyl or pyridylmethyl, in each case optionally substituted in the aryl or heteroaryl part once or twice by identical or different substituents, wherein the substituents are:
fluorine, chlorine, bromine, methyl, ethyl, n- or i-propyl, methoxy, ethoxy, n- or i-propoxy, trifluoromethyl, difluoromethyl, trifluoromethoxy or difluoromethoxy and $R^5$ represents methyl, ethyl, n- or i-propyl, n-, i-, s- or t-butyl or allyl, or represents benzyl which is optionally substituted in the aryl part once or twice by identical or different substituents, wherein the substituents are:
fluorine, chlorine, bromine, methyl, ethyl, n- or i-propyl, methoxy, ethoxy, n- or i-propoxy, trifluoromethyl, difluoromethyl, trifluoromethoxy or difluoromethoxy, or $R^4$ and $R^5$, together with the nitrogen atom to which they are bonded, represent a pyrrolidinyl, piperidinyl, perhydroazepinyl, piperazinyl or morpholinyl radical which is optionally substituted once or twice, wherein the substituents are:
chlorine, methyl, ethyl, methoxy or ethoxy.

4. A 1,2,4-dithiazolium salt of the formula

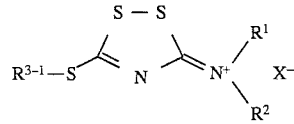

in which
$R^1$ represents aryl having 6 to 10 carbon atoms which is optionally substituted once or several times by identical or different substituents, wherein the substituents are:
halogen, cyano, nitro, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl parts and phenyl which is optionally substituted once or several times by identical or different substituents wherein the substituents are halogen and/or straight-chain or branched alkyl and/or straight-chain or branched alkoxy and/or straight-chain or branched halogenoalkyl and/or straight-chain or branched halogenoalkoxy having in each case 1 to 4 carbon atoms and, optionally, 1 to 9 identical or different halogen atoms, and $R^2$ represents straight-chain or branched alkyl having 1 to 8 carbon atoms, or $R^1$ and $R^2$, together with the nitrogen atom to which they are bonded, represent a saturated five- to seven-membered heterocyclic radical which is optionally substituted once or several times by identical or different substituents and optionally contains further heteroatoms selected from the group consisting of particular nitrogen, oxygen and sulphur wherein the substituents are:
halogen, in each case straight-chain or branched alkyl or alkoxy having in each case 1 to 4 carbon atoms or in each case straight-chain or branched halogenoalkyl or halogenoalkoxy having in each case 1 to 4 carbon atoms and 1 to 9 identical or different halogen atoms, and X represents the anion of an inorganic acid, and wherein $R^{3-1}$ represents aralyalkyl having 6 to 10 carbon atoms in the aryl
alkyl having 6 to 10 carbon atoms in the aryl part and 1 to 4 carbon atoms in the straight-chain or branched alkyl part or heteroarylalkyl having 2 to 9 carbon atoms and 1 to 3 identical or different heteroatoms selected from the group consisting of nitrogen, oxygen and sulphur in the heteroaryl part and 1 to 4 carbon atoms in the straight-chain or branched alkyl part, in each case optionally substituted in the aryl or heteroaryl part once or several times by identical or different substituents, wherein the substituents are:
halogen, cyano, nitro, carbamoyl, in each case straight-chain or branched alkyl, alkoxy or alkoxycarbonyl having in each case 1 to 4 carbon atoms or in each case straight-chain or branched halogenoalkyl or halogenoalkoxy having in each case 1 to 4 carbon atoms and 1 to 9 identical or different halogen atoms.

5. A TNF-α-inhibiting composition comprising an amount effective therefore of a 1,2,4-dithiazolium salt according to claim 4 and a pharmalogically acceptable diluent.

6. A method of inhibiting TNF-α in a patient in need thereof which comprises administering to such patient an amount effective therefor of a 1,2,4-dithiazolium salt according to claim 4.

* * * * *